United States Patent [19]

Nadelson

[11] 4,024,283

[45] May 17, 1977

[54] THIODIMETHYLENE BIS(PIVALOPHENONE)

[75] Inventor: Jeffrey Nadelson, Lake Parsippany, N.J.

[73] Assignee: Sandoz, Inc., E. Hanover, N.J.

[22] Filed: Aug. 15, 1975

[21] Appl. No.: 605,070

[52] U.S. Cl. .......................... 424/331; 260/590 D; 260/592

[51] Int. Cl.$^2$ ................. C07C 49/76; A61K 31/12

[58] Field of Search .......... 260/592, 608 R, 609 D, 260/590 D; 424/331

[56] References Cited

UNITED STATES PATENTS

| | | | |
|---|---|---|---|
| 1,842,414 | 1/1932 | Leaper | 260/609 |
| 2,402,640 | 6/1946 | Lazier et al. | 260/609 |
| 2,445,939 | 7/1948 | Cook et al. | 260/592 |
| 2,456,588 | 12/1948 | Loverde | 260/608 |
| 2,507,111 | 5/1950 | Lieber | 260/592 |
| 3,884,961 | 5/1975 | Houlihan et al. | 260/592 |

OTHER PUBLICATIONS

Reid, Organic Chemistry of Bivalent Sulfur, vol. II, pp. 18–19 (1960).

*Primary Examiner*—James O. Thomas, Jr.
*Assistant Examiner*—James H. Reamer
*Attorney, Agent, or Firm*—Gerald D. Sharkin; Robert S. Honor; Timothy G. Rothwell

[57] ABSTRACT

Substituted or unsubstituted thiodimethylene bis(pivalophenone), e.g., 4',4'''-(thiodimethylene) bis(pivalophenone) are prepared by treating a corresponding α-halo-p-tert-alkanoyl toluene with an alkali metal sulfide and are useful as hypolipidemic agents.

7 Claims, No Drawings

THIODIMETHYLENE BIS(PIVALOPHENONE)

This invention relates to substituted or unsubstituted thiodimethylene bis(pivalophenone) and to their preparation.

The compounds of this invention may be represented by the following structural formula

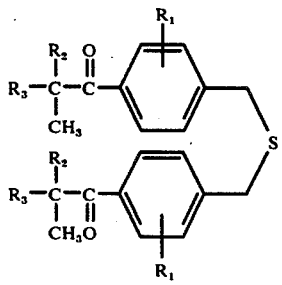

wherein
$R_1$ represents hydrogen, or halo having an atomic weight of about 19 to 36, i.e. fluoro or chloro, and $R_2$ and $R_3$ each independently represent lower alkyl having 1 to 2 carbon atoms, i.e. methyl or ethyl.

The compounds of formula (I) are prepared according to the following reaction scheme:

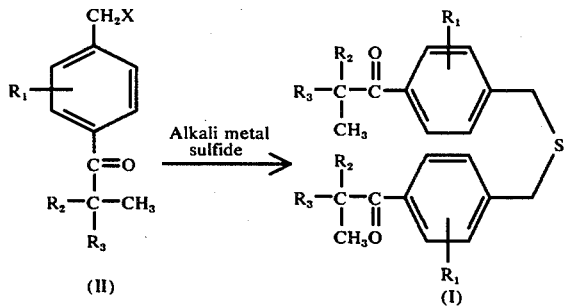

where
X represents chlorine or bromine, and
$R_1$, $R_2$ and $R_3$ are as defined above.

The compounds of formula (I) are prepared by treating a compound of the formula (II) with an alkali metal sulfide such as sodium sulfide, potassium sulfide and the like, preferably sodium sulfide, in the presence of a water-miscible solvent and water. Although the particular water-miscible solvent employed is not critical, it is preferred that the reaction be run in the presence of dimethylformamide, dimethylacetamide, dimethylsulfoxide and the like or acetone, preferably dimethylformamide. The temperature of the reaction is not critical, but it is preferred that the reaction be run from about 50° to 200° C., preferably the boiling point of the solvent mixture employed. The reaction is run from about 12 to 36 hours, preferably from about 18 to 22 hours. The product is recovered using conventional techniques, e.g. recrystallization.

The compounds of formula (II) are prepared according to the following reaction scheme:

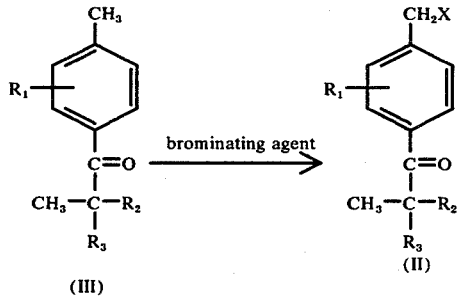

where $R_1$, $R_2$, $R_3$ and X are as defined above.

The compounds of formula (II) are prepared by treating a compound of formula (III) with a halogenating agent in the presence of an inert organic solvent and free radical initiator. The halogenating agent which can be used is bromine, N-bromosuccinimide, N-bromo phthalamide, N-bromo-acetamide, chlorine, N-chlorosuccinimide and the like. The particular agent used is not critical, but N-bromosuccinimide is preferred. In the preferred process, the free radical initiator used is an organic peroxide, especially benzoyl peroxide. The reaction can also be carried out under ultraviolet light. Although the particular solvent used is not critical, the preferred solvents are the halogenated hydrocarbons such as methylenedichloride, chloroform, carbon tetrachloride and the like, although the aromatic hydrocarbons such as benzene, toluene and the like can also be employed. The temperature of the reaction is not critical, but reflux temperature of the solvent is preferred. The reaction is run for about 12 to 48 hours; preferably about 18 to 25 hours. The product is recovered by conventional techniques, e.g., crystallization.

Many of the compounds of formula (III) are known and may be prepared by methods described in the literature. The compounds of formula (III) not specifically described may be prepared by analogous methods from known starting materials.

The compounds of formula (I) are useful because they possess pharmaceutical activity as hypolipidemic agents, as indicated by the fall in cholesterol and triglyceride levels in male albino Wistar rats weighing 110–130 g. initially. The rats are maintained on drug-free laboratory chow diet for 7 days and then divided into groups of eight to 10 animals. Each group with the exception of the control is then given orally 120 milligrams per kilogram of body weight per diem of the compound for 6 days. At the end of this period, the animals are anesthetized with sodium hexobarbital and bled from the carotid arteries. Serum or plasma samples are collected, and 1.0 ml. samples of the serum are added to 9.0 ml. redistilled isopropanol. Two autoanalyzer cupsful of a mixture of zeolite-copper hydroxide and Lloydds reagent (Kessler, G., and Lederer, H., 1965, Technicon Symposium, Mediad Inc., N.Y., (345–347) are added, and the mixture is shaken for 1 hour. Cholesterol and triglyceride levels are determined simultaneously on the same sample by Technicon N 24 A (cholesterol) and N-78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such usage, the compounds (I) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups, and elixirs and parenterally as solutions, suspensions, dispersions, emulsions and the like, e.g., a sterile injectable aqueous solution. The dosage will vary depending upon the mode of administration utilized and the particular compound employed.

The hypolipidemic effective dosage of these active compounds in the alleviation of lipidemia may vary depending on the particular compound employed and the severity of the condition being treated. However, in general, satisfactory results are obtained when the compounds of formula (I) are administered at a daily dosage of from about 4.0 milligrams of about 250 milligrams per kilogram of animal body weight, preferably given in divided doses two to four times a day, or in sustained release form. For most large mammals, the total daily dosage is from about 300 milligrams to about 1500 milligrams. Dosage forms suitable for internal use comprise from about 75.0 to about 750 milligrams of the active compound in intimate admixture with a solid or liquid pharmaceutically acceptable carrier of diluent.

A representative formulation suitable for oral administration two to four times a day for the treatment of lipidemia is a capsule prepared by standard encapsulating techniques which contains the following:

| INGREDIENTS | WEIGHT (mg.) |
| --- | --- |
| 4',4'''-(thiodimethylene) bis(pivalophenone) | 150 |
| inert solid diulent (starch, lactose, kaolin) | 300 |

A preferred aspect of this invention concerns compound (I) wherein $R_1$ represents hydrogen and $R_2$ and $R_3$ represent methyl.

EXAMPLE 1

α-bromo-p-pivaloyl toluene

To a suspension of 28.5 g. (1.17 g. atoms) magnesium turnings in 150 ml. tetrahydrofuran under a nitrogen atmosphere there is added 10 ml. of 4-bromo toluene (1.17 mole) in 650 ml. dry tetrahydrofuran; the reaction is started and the remainder of the bromo toluene solution is added dropwise at a rate that maintains a moderate reflux. After the addition is complete, the mixture is refluxed for an additional 1½ hours. The resulting Grignard solution is added dropwise to a cold solution of 128.0 g. pivaloyl chloride (1.06 mole) in 500 ml. dry tetrahydrofuran at a rate that maintains the temperature at 0° to −5° C. The solution is stirred for an additional 1½ hours at 0° C. and then at room temperature for 18 hours. The mixture is then cooled to 0° C. and hydrolyzed by the addition of 100 ml. 2N hydrochloric acid. The layers are separated and 200 ml. of ether is added to the organic phases which is then washed respectively with 100 ml. 2N hydrochloric acid, 100 ml. 10% sodium bicarbonate solution, and 100 ml. saturated sodium chloride. The resulting layer is dried over anhydrous sodium sulfate, filtered, and the solvent is removed in vacuo to give p-pivaloyl toluene (b.p. 80° to 84° C./0.7 mm, $n_C^{21}$1.5108). A mixture of 156.3 g. (0.886 mole) of the resulting p-pivaloyl toluene is then added to 157.8 g. (0.886 mole) N-bromosuccinimide, 4.0 g. (0.016 mole) benzoyl peroxide and 150 ml. carbon tetrachloride and heated at reflux for 18 hours. The mixture is cooled and filtered and the resulting oil is distilled in vacuo to give α-bromo-p-pivaloyl toluene (b.p. 124°–132° C/0.7 mm, $n_D^{22}$1.5546-V.P.C. 96% monobromo 4%-dibromo).

Following the above procedure and using in place of 4-bromo-toluene equivalent amounts of:
a. 4-bromo-2-chlorotoluene, or
b. 4-bromo-2-fluorotoluene,
there is obtained.
a. α-bromo-2-chloro-4-pivaloyl toluene, or
b. α-bromo-2-fluoro-4-pivaloyl toluene, respectively.

EXAMPLE 2

4',4'''-(thiodimethylene) bis(pivalophenone)

A solution of 20.0 g. (0.078 mole) of α-bromo-p-pivaloyl toluene in 40 ml. dimethylformamide is warmed to 50° C. and treated dropwise with 9.4 g. (0.0392 mole) of sodium sulfide nonahydrate in 11 ml. water for about 15 minutes. The resulting solution is refluxed for 18 hours, cooled and poured onto 1 liter of ice/water. The aqueous solution is extracted twice with ether and the ether washed with water and saturated sodium chloride solution, dried over anhydrous magnesium sulfate and evaporated. The residue is recrystallized from methanol to give 4',4'''-(thiodimethylene) bis(pivalophenone); m.p. 64°–65° C.

Following the above procedure and using in place of α-bromo-p-pivaloyl toluene an equivalent amount of
a. α-bromo-2-chloro-4-pivaloyl toluene, or
b. α-bromo-2-fluoro-4-pivaloyl toluene,
there is obtained
a. 3',3'''-dichloro-4',4'''-(thiodimethylene) bis (pivalophenone), or
b. 3',4'''-difluoro-4',4'''-(thiodimethylene) bis (pivalophenone), respectively.

The 4',4'''-(thiodimethylene) bis(pivaloyphenone) of this example is an effective hypolipidemic agent when oraly administered to an animal suffering from lipidemia at a dosage of 150 mg. four times per day.

What is claimed is:

1. A compound of the formula

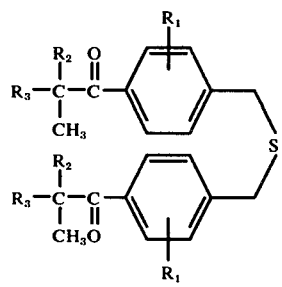

where
$R_1$ represents hydrogen, halo having an atomic weight of about 19 to 36, and
$R_2$ and $R_3$ each independently represent lower alkyl having 1 to 2 carbon atoms.

2. A compound of the formula

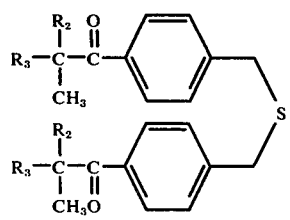

where
R_2 and R_3 are as defined in claim 1.

3. A compound of the formula

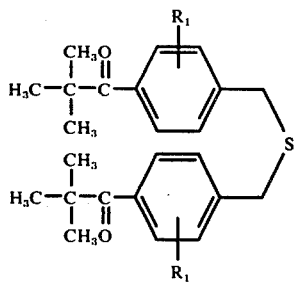

where
R_1 is as defined in claim 1.

4. The compound of claim 1 wherein R_1 is hydrogen and R_2 and R_3 each represent methyl.

5. The compound of claim 1 which is 4',4'''-(thiodimethylene) bis(pivalophenone).

6. A pharmaceutical composition comprising a hypolipidemic effective amount of a compound of claim 1 and a pharmaceutically acceptable diluent or carrier therefor.

7. A method of treating lipidemia which comprises administering to a mammal in need of said treatment a hypolipidemic effective amount of a compound of claim 1.

* * * * *